United States Patent [19]
Gehl

[11] Patent Number: 6,113,635
[45] Date of Patent: *Sep. 5, 2000

[54] EPITHESIS

[76] Inventor: Gerolf Gehl, Zürichstreet 56, CH-8700 Kusnacht, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/886,728

[22] Filed: Jul. 1, 1997

[51] Int. Cl.$^7$ ........................................................ A61F 2/52
[52] U.S. Cl. .................................. 623/7; 623/8; 264/222
[58] Field of Search .............................. 623/7, 8; 450/38, 450/39, 40, 54, 55; 264/44, 222; 156/145

[56] References Cited

U.S. PATENT DOCUMENTS

| | | | |
|---|---|---|---|
| 4,125,117 | 11/1978 | Lee | 128/481 |
| 4,404,296 | 9/1983 | Schapel | 523/105 |
| 4,681,587 | 7/1987 | Eberl et al. | 627/7 |
| 5,022,942 | 6/1991 | Yan et al. | 623/7 |
| 5,133,754 | 7/1992 | Laghi | 623/8 |
| 5,437,824 | 8/1995 | Carlisle et al. | 623/11.11 |
| 5,658,330 | 8/1997 | Carlisle et al. | 623/8 |
| 5,697,974 | 12/1997 | Wang | 627/7 |
| 5,733,335 | 3/1998 | Ishikawa et al. | 623/7 |

*Primary Examiner*—David H. Willse
*Assistant Examiner*—Sozette J. Jackson
*Attorney, Agent, or Firm*—Fulbright & Jaworski L.L.P

[57] ABSTRACT

The invention relates to an epithesis consisting of a sheath adapted to a body part on the back and simulating the desired body surface on the front, and a filling inside the sheath, wherein the filling consists of an elastic material with a density of d<0.25 g/cm$^3$.

9 Claims, No Drawings

EPITHESIS

CROSS-REFERENCE TO RELATED APPLICATION not applicable

STATEMENT REGARDING FEDERALLY SPONSORED RESEARCH OR DEVELOPMENT not applicable

REFERENCE TO A "MICROFICHE APPENDIX"

not applicable

BACKGROUND OF THE INVENTION (1) Field of the Invention

This invention relates to an epithesis consisting of a sheath adapted to a body part on the back and simulating the desired body surface on the front, and a filling inside the sheath.

(2) Description of the Related Art Including Information Disclosed Under 37 C.F.R. 1.97 and 1.98

Epitheses for compensating congenital or acquired physical defects have been known for some time and described often. They are widely used in order to mask the results of accidents or surgical operations and simulate a natural body surface. A frequent purpose is to simulate the female breast after surgical removal due to malicious tumors.

Epitheses serve firstly to protect the defective body surface against undesirable external influences, for example to support wound healing and improve hygiene. Secondly epitheses are prescribed and worn in particular for cosmetic reasons.

In view of the purpose at hand it is necessary to adapt the epithesis optimally to the body surface. Only in this way can the basic medical and hygienic conditions be fulfilled, and only in this way can the necessary "wearing comfort" be ensured. In addition, only a well fitting epithesis arouses the desired optical impression and allows the patient to move with ease. Optimal simulation of the desired body surface is taken for granted, including simulation of the natural skin color.

Conventional epitheses consist of an outer sheath adapted to the body surface and filled with a liquid. The sheath material usually consists of silicone rubber or a polyurethane plastic, both of which have proven exceptionally skin-compatible. The filling frequently consists of liquid silicone. The liquid filling ensures a certain deformability via the sheath likewise made of an elastic material.

A disadvantage of these known epitheses has proven to be the relatively high weight, however. This relatively high weight necessitates special measures for attaching the epithesis, which make its design more elaborate than is normally felt to be pleasant. This, and the high weight, lead to an impairment of mobility and also cause the epithesis to slip in case of greater exercise. Further, there is a danger of leakage if the sheath is damaged. Air-filled epitheses collapse if the sheath is damaged. In both cases, repair and lasting restoration are not easy.

BRIEF SUMMARY OF THE INVENTION

The invention is based on the problem of providing a material for filling the epithesis which avoids the above-described disadvantages but is completely safe medically, skin-compatible in case it passes through the sheath or the sheath is damaged, and able to give the epithesis the elasticity of the natural skin surface. In addition the epithesis should remain dimensionally stable over long time periods.

DETAILED DESCRIPTION OF THE INVENTION

This problem is solved with a filling consisting of an elastic material with a density $d<0.25$ g/cm$^3$.

What is essential is that the filling is adjusted elastically, i.e. can yield to pressure in itself up to a certain degree without causing the epithesis to slip. The use of liquids in known epitheses does not ensure this elasticity since liquids are virtually incompressible and always strive to yield laterally passing on the pressure. The materials used according to the invention, by contrast, are so elastic that the exerted pressure can be absorbed at least partly by the filling material.

BRIEF DESCRIPTION OF THE SEVERAL VIEWS OF THE DRAWING(S)

not applicable

DETAILED DESCRIPTION OF THE INVENTION

It has proved suitable to use flock and foam particles which are introduced into the sheath and yield to pressure in themselves, but also remove part of the pressure laterally through lateral displacement of the particles. However, it is especially suitable to use a filling consisting of just one integrated foam part. Although such a tight foam filling cannot be displaced laterally, it yields in itself. This foam part consists expediently of silicone foam, although polyurethane foams can also be used. In this case it is advantageous to incorporate the foam part integrally, i.e. to produce the foam part within the sheath by introducing a foaming agent so as to ensure complete foaming.

Materials to be used for this purpose are basically known two-component silicone foaming agents consisting of a silicone component and a catalyst. Mixing the two components gives rise to the desired foam within a short time. If the two components are introduced into the sheath directly after mixing, the foam arises in the sheath itself, filling it completely and "tightly". A suitable material is for example "Prosthetic Foam A-2380" (silicone foam elastomer base) from the firm Silicon in Lakeside, Ariz., USA. The corresponding catalyst is sold by the same firm under the designation A-2380 catalysts.

The sheath material consists of a skin-compatible, medically tested silicone rubber which is dyeable and commercially available. The rubber characteristically has a Shore hardness of 20 A. A useful material is sold for example by the firm Orthomax, United Kingdom.

Since the inventive epitheses have a porous filling they have an extremely low weight. It is readily possible to control the weight by influencing the degree of porosity. Since no liquid filling is present, leakage is impossible, as can happen in conventional epitheses for example as a consequence of many years' use or mechanical stress. Collapse is equally impossible, as can happen in known air-filled "floating prostheses".

The inventive epitheses are produced using the following steps:

producing the sheath using a body impression, the sheath being equipped with the openings necessary for filling;

introducing the filling consisting of an elastic material with a density of d<0.25 g/cm³;

sealing the at least one opening with a stopper.

If the filling consists of fibers or particles, these particles or fibers are introduced into the interior of the epithesis sheath through the existing opening and compacted there by vibrating. If a foaming agent is used, however, it is expedient to produce an integral foamed-in silicone foam part in the interior of the sheath. This is done by injecting the inter-reacting compound of foaming agent and catalyst or reactive second component into the interior of the sheath and letting it react there. This results in a foam part tightly filling the sheath and giving the epithesis the desired elasticity. By using suitable catalysts one can also cause the silicone foam formed in the interior to connect reactively with the silicone rubber sheath, which makes the epithesis appear very tight, as is expedient for example for use in the area of the calves. Depending on the manner of introducing the foaming agent, it can be necessary to provide the epithesis sheath with a plurality of openings for pressure compensation. For foaming with the foaming agent, cuvetting is expedient, i.e. embedding the sheath in a mold in order to absorb the foaming pressure and stabilize the outer form.

After foaming takes place in the sheath, the openings present in the sheath are sealed with suitable stoppers made for example of silicone rubber, whereby it is useful to have the stoppers bond with the sheath material in order to ensure that the contents are sealed in.

The inventive epitheses are primarily used for correcting the appearance of the female breast after operations. However, they can also be used for other parts of the body, for example in the area of the buttocks, the waist or the calves. Breast epitheses are expediently worked into the bra, the corsetry or the swimsuit, thereby ensuring a proper fit.

What is claimed is:

1. A low weight epithesis consisting of a sheath adapted to a body part on its back and simulating a desired body surface on its front, and a filling inside the sheath, wherein the filling consists of a foamed-in elastic foam part with a density of d<0.25 g/cm³, prepared by injecting a 2-component silicon foaming agent into the sheath, the sheath being embedded in a mould in order to stabilize its outer form during the foaming process.

2. The epithesis of claim 1, wherein the filling consists of flock, foam particles or a foam part.

3. The epithesis of any of claims 1, wherein the sheath consists of skin-compatible silicone rubber or polyurethane (plastic).

4. A breast epithesis according to claims 1.

5. A method for producing the epithesis of claim 1 which includes the following steps:

producing a sheath using a body impression, the sheath being equipped with at least one opening necessary for filling;

embedding the sheath in a mould in order to stabilize its outer form;

introducing the filling consisting of an elastic material with a density of d<0.25 g/cm³ by injecting a 2-component silicone foaming agent;

sealing the at least one opening with a stopper.

6. The method of claim 5, wherein the sheath is filled with flock, foam particles or a foaming agent.

7. The method of claim 5, wherein the filling consists of a two-component silicone foaming agent which foams out the sheath from inside out.

8. The method of claims 5, wherein the sheath is sealed with a stopper made of silicone plastic which is bonded with the surrounding sheath material.

9. A breast epithesis according to claim 3.

* * * * *